US005510507A

United States Patent [19]
Ayers et al.

[11] Patent Number: 5,510,507
[45] Date of Patent: Apr. 23, 1996

[54] SELECTIVE ASYMMETRIC HYDROGENATION OF DEHYDROAMINO ACID DERIVATIVES USING RHODIUM AND IRIDIUM DIPHOSPHINITE CARBOHYDRATE CATALYST COMPOSITIONS

[75] Inventors: Timothy A. Ayers; Thaliyil V. Rajanbabu, both of Wilmington, Del.

[73] Assignee: E. I. Du Pont de Nemours and Company, Wilmington, Del.

[21] Appl. No.: 427,327

[22] Filed: Apr. 24, 1995

Related U.S. Application Data

[62] Division of Ser. No. 179,859, Jan. 11, 1994, Pat. No. 5,481,006.

[51] Int. Cl.$^6$ .................................................. C07C 229/34
[52] U.S. Cl. .............................. 560/41; 560/39; 562/444; 562/449; 562/450; 549/77; 549/76
[58] Field of Search ........................ 560/41, 39; 562/444, 562/449, 450; 549/77, 76

[56] References Cited

U.S. PATENT DOCUMENTS

| | | | |
|---|---|---|---|
| 4,010,181 | 3/1977 | Aviron-Violet | 260/326.14 |
| 4,879,398 | 11/1989 | Getman et al. | 556/413 |
| 5,099,077 | 3/1992 | Petit et al. | 568/814 |

FOREIGN PATENT DOCUMENTS

| | | | |
|---|---|---|---|
| 1027141 | 2/1978 | Canada | 260/565 |
| 0443923 | 2/1991 | European Pat. Off. | C07F 9/46 |
| 0512416 | 1/1992 | European Pat. Off. | C07F 9/572 |
| 0498507 | 2/1992 | European Pat. Off. | C07C 231/18 |

(List continued on next page.)

OTHER PUBLICATIONS

Jackson, W. R. et al, *Aust. J. Chem.*, 35, 2069–2075, 1982.
Wink, D. J. et al, *Inorg. Chem.*, 29 5006–5008, 1990.
Selke, R. et al, *J. of Molecular Catalysis*, 37, 213–225, 1986.
Selke, R. et al, *J. of Molecular Catalysis*, 56, 315–328, 1989.
Rajanbabu, T. V. et al., *J. Am. Chem.*, 114, 6265–6266, 1992.
Selke, R., *React. Kinet. Catal. Lett.*, 10(2), 135–138, 1979.
Jackson, R et al, *J. of Organometallic Chem.*, 159, C29–C31, 1978.
Cullen, W. R. et al, *Tetrahedron Lett.*, No. 19, 1635–1636, 1978.
Selke, R., *J. of Molecular Catalysis*, 37, 227–234, 1986.
Selke, R., *J. f. prakt. Chemie*, Band 329, Heft, 4, 717–724, 1987.
Selke, R. et al, *Tetrahedron: Asymmetry*, 4(3), 369–382, 1993.
Johnson, T. H. et al, *J. Org. Chem.*, 44(11), 1878–1879, 1979.
Johnson, T. H. et al, *J. Org. Chem.*, 45, 62–65, 1980.
Johnson, T. H. et al, *J. of Molecular Catalysis*, 9, 307–311, 1980.
Habus, I. et al, *J. of Molecular Catalysis*, 42, 173–178, 1987.
Capka, M. et al, *React. Kinet. Catal. Lett.*, 10(3), 225–228, 1979.
Selke, R., *React. Kinet. Catal. Lett.*, 10(2), 135–138, 1979.
Selke, R., *J. of Organometallic Chemistry*, 370, 241–248, 1989.
Selke, R., *J. of Organometallic Chemistry*, 370, 249–256, 1989.
Selke, R. et al, *J. of Molecular Catalysis*, 56, 315–328, 1989.
Brunner, H. et al, *J. Chem. Research (S)*p. 76, 1980.
Bourson, J. et al, *J. of Organometallic Chemistry*, 229, 77–84, 1982.
Sunjic, V. et al, *Gazetta Chimica Italiana*, 119, 229–233, 1989.
Yamashita, M. et al, *Bull. Chem. Soc. Jpn.*, 62, 942–944, 1989.
Nakamura, Y. et al, *Chemistry Letters*, pp. 7–10, 1980.
Yamada, M. et al, *Carbohydrate Research*, 95, C9–C12, 1981, Elsevier Scientific Pub. Co., Amsterdam.
Yamashita, M. et al, *Bull. Chem. Soc. Jpn.*, 55, 2917–2921, 1982.
Saito, S. et al, *Chem. Pharm. Bull.*, 33(12), 5284–5293, 1985.
Yamashita, M. et al, *Bull. Chem. Soc. Jpn.*, 59, 175–178, 1986.
Cesarotti, E. et al, *Gazetta Chimica Italiana*, 117, 129–133, 1987.
Habus, I. et al, *CCACAA*, 61(4), 857–866, 1988.
Hatat, C. et al, *Tetrahedron Letters*, 29(30), 3675–3578, 1988.
Dobler, Chr. et al, *J. of Organometallic Chemistry*, 344, 89–92, 1988.
Krause, H. W. et al, *New Journal of Chemistry*, 13(8–9), 1989.
Sunjic, V. et al., *J. of Organometallic Chemistry*, 370, 295–304, 1989.
Hatat, C. et al, *Tetrahedron Letters*, 31(29), 4139–4142, 1990.
Taudien, S. et al, *Tetrahedron: Asymmetry*, 4(1), 73–84, 1993.
Parrinella, G. et al, *J. Am. Chem. Soc.*, 109, 7122–7127, 1987.
Mortreaux, A. et al, *Bulletin De La Societe Chimique de France*, No. 4, 631–639, 1987.
Toth, I. et al, *Organimetallics*, 12, 848–852, 1993.
Morimoto, T. et al., *Chem. Pharm. Bull.*, 40(10), 2894–2896 (1992).
Onuma, K. et al., *Tetrahedron Letters*, 34, 3163–3166 (1979).

*Primary Examiner*—José G. Dees
*Assistant Examiner*—Samuel Barts

[57] ABSTRACT

A process and catalyst composition are provided for the highly efficient enantioselective hydrogenation of dehydroamino acid derivatives. The catalyst composition comprises rhodium or iridium and a diphosphinite carbohydrate ligand, wherein the phosphorous atoms are attached to aromatic groups substituted with electron-donating substituents. Also provided is a means to selectively produce α amino acids in either the L or the D form, based upon use of a sugar in the ligand with phosphinites attached in an absolute Right-Left or Left-Right configuration, respectively.

11 Claims, No Drawings

FOREIGN PATENT DOCUMENTS

| | | | |
|---|---|---|---|
| 7243479 | 8/1974 | France | C07C 45/00 |
| 280528 | 3/1989 | Germany | C07C 101/04 |
| 280529 | 3/1989 | Germany | C07C 101/04 |
| 280527 | 3/1989 | Germany | C07C 101/04 |
| 275623 | 1/1990 | Germany | B01J 31/18 |
| 280474 | 7/1990 | Germany | B01J 31/18 |
| 280473 | 7/1990 | Germany | B01J 31/18 |
| 1389802 | 3/1973 | United Kingdom | C07C 45/08 |
| WO93/03839 | 3/1993 | WIPO | B01J 31/24 |

SELECTIVE ASYMMETRIC HYDROGENATION OF DEHYDROAMINO ACID DERIVATIVES USING RHODIUM AND IRIDIUM DIPHOSPHINITE CARBOHYDRATE CATALYST COMPOSITIONS

This is a division of application Ser. No. 08/179,859, filed Jan. 11, 1994 now U.S. Pat. No. 5,481,006.

FIELD OF THE INVENTION

This invention relates to a process and catalyst composition for the asymmetric hydrogenation of dehydroamino acid derivatives to selectively produce either D or L amino acid compounds. The process utilizes a catalyst composition comprising rhodium or iridium and a diphosphinite carbohydrate ligand, wherein the ordered absolute configuration of the two phosphinite groups on the carbohydrate determines whether the α amino acids produced will be D or L. Further, the ligands of the invention comprising phosphinite groups which have aromatic groups substituted with electron-donating substituents, result in catalysts which display very efficient enantioselectivity during the hydrogenation reaction.

BACKGROUND OF THE INVENTION

The subject of asymmetric hydrogenation, especially using dehydroamino acid derivatives as substrates, is a commercially important area, particularly in the pharmaceutical field.

Cullen reported the use of the 2,3-glucopyranose system for asymmetric hydrogenation of dehydroamino acid derivatives in 1978 (Tetrahedron Lett. 1978, 1635). Similar disclosures were made by Thompson (J. Organometal. Chem. 1978, 159, C29; U.K. 41,806,177 Jul. 10, 1977).

Jackson and Thompson (J. Organomet. Chem. 1978, 159, C29) describe the use of 2,3-diphenylphosphinites of a "D-glucopyranose" for S-phenylalanine and 4,6-diphenylphosphinite of a "D-xylofuranose" for the corresponding R amino acid. Thus, unlike the present invention, in order to make R and S amino acid derivatives altogether different sugar back bones were previously employed. Habus, Raza and Sunjic (J. Mol. Cata. 1987, 42, 173) also report similar results using "D-glucopyranose" and "D-xylopyranose"-derived bis-diphenylphosphinites for the synthesis of R and S-phenylalanine derivatives. The enantioselectivity in each case is low and in contrast to the present invention, reaction conditions are not practical for large scale preparation of these compounds, where high selectivity is needed.

Selke et al. began work in this area in 1978 and has published a series of papers and also patented some of this work. (J. Mol. Catal. 1986, 37, 213, 227; J. Prakt. Chem. 1987, 329(4), 717; J. Mol. Catal. 1989, 56, 315; DD 140 036; DD 240 372; and DD 248 028). Similar to Cullen and Thompson, Selke discloses using a phenyl group on the phosphorus. Unlike Applicants' process, however, the phosphorus phenyl group was unsubstituted and no recognition was disclosed of enhanced enantioselectivity as a function of electron-rich substituents on the phenyl. Further, the Selke, Cullen and Thompson disclosures are limited to ligands using "2,3-dideoxyglucopyranose", "mannopyranose" and "galactopyranose" in systems yielding only S amino acid derivatives.

Other sugar diphosphinites have been examined in both rhodium (J. Org. Chem. 1980, 45, 62) and ruthenium (J. Mol. Catal. 1980, 9, 307) catalyzed hydrogenation reactions. However, low ee's were obtained. Some simple derivatives have also been reported by Sunjic (Sunjic: J. Mol. Catal. 1987, 42, 173); again, in processes yielding low ee values.

Other references disclose carbohydrates as the chiral auxiliary for monophosphinites (Yamashita: Carbohydrate Res. 1981,95 C9; Bull. Chem. Soc. Jpn. 1982, 55, 2917; Bull. Chem. Soc. Jpn. 1986, 59, 175) and phosphines (Sunjic: J. Organometal.Chem. 1989, 370, 295; Nakamura: Chem. Lett. 1980, 7).

Aminophoshine-phosphinites from readily available amino acids have also been used as ligands for asymmetric hydrogenations. (U.S. Pat. No. 5,099,077, Mar. 24, 1992; Petit, M.; Mortreaux, A.; Petit, F.; Buono, G.; Peiffer, G. Nou. J. Chem. 1983, 593.)

SUMMARY OF THE INVENTION

The present invention provides a process for asymmetric hydrogenation, comprising:

reacting a dehydroamino acid derivative of formula I $$ZZC=C(CO_2Z)(NHZ) \qquad I$$

wherein each Z is independently H or a $C_1$ to $C_{40}$ carboalkoxy, $C_1$ to $C_{40}$ aromatic or nonaromatic hydrocarbyl or $C_1$ to $C_{40}$ aromatic or nonaromatic heterocyclic radical; optionally substituted with one or more halo, alkoxy, carboalkoxy, nitro, haloalkyl, hydroxy, amido, keto, or sulfur containing groups;

with a source of hydrogen;

in the presence of a catalyst composition comprising iridium or rhodium and a chiral, nonracemic diphosphinite ligand of formula II $$(R^1)_2\text{—P—X—R}^2\text{—X—P—}(R^1)_2 \qquad II$$

wherein $R^2$ is a $C_4$ to $C_{40}$ dideoxycarbohydrate;

each X is independently O or $NR^3$, wherein $R^3$ is H, a $C_1$ to $C_{20}$ alkyl or aryl; and each $R^1$ is independently an aromatic hydrocarbyl substituted with one or more amino, dialkylamino, hydroxy, alkoxy, alkyl, triarylsilyl, or trialkylsilyl groups, or an aromatic heterocycle substituted with one or more amino, dialkylamino, hydroxy, alkoxy, alkyl, trialkysilyl, or triarylsilyl groups;

to yield a chiral, nonracemic mixture of compounds of formula III $$ZZCH\text{—}CH(CO_2Z)(NHZ) \qquad III$$

wherein Z is defined as above.

This invention further provides a method for predicting whether the above hydrogenation process will yield an R or S amino acid derivative, based upon whether the absolute configuration of the phosphinite groups "X" attached to the carbohydrate $R^2$ are configured in Right-Left configuration to yield the S amino acid derivation of Formula III, or are configured in a Left-Right configuration to yield the R amino acid derivative of Formula III.

This invention further provides a catalyst composition comprising iridium or rhodium and a chiral, nonracemic diphosphinite ligand of formula II $$(R^1)_2\text{—P—X—R}^2\text{—X—P—}(R^1)_2 \qquad II$$

wherein $R^2$ is a $C_4$ to $C_{40}$ dideoxycarbohydrate;

each X is independently O or $NR^3$, wherein $R^3$ is H, a $C_1$ to $C_{20}$ alkyl or aryl; and each $R^1$ is independently an aromatic hydrocarbyl substituted with amino, dialkylamino, hydroxy, alkoxy, alkyl, trialkylsilyl, or triarylsilyl groups or an aromatic heterocycle substituted with amino, dialkylamino, hydroxy, alkoxy, alkyl, trialkysilyl, or triarylsilyl groups.

This invention further provides a process for asymmetric hydrogenation comprising reacting a dehydroamino acid derivative of formula I $$ZZC=C(CO_2Z)(NHZ) \qquad \text{I}$$

wherein each Z is independently H or a $C_1$ to $C_{40}$ carboalkoxy, $C_1$ to $C_{40}$ aromatic or nonaromatic hydrocarbyl or $C_1$ to $C_{40}$ aromatic or nonaromatic heterocyclic radical, optionally substituted with one or more halo, alkoxy, carboalkoxy, nitro, haloalkyl, hydroxy, amido, keto or sulfur containing groups;

with a source of hydrogen;

in the presence of a catalyst composition comprising iridium or rhodium and a chiral nonracemic diphosphinite ligand of formula II $$(R^1)_2-P-X-R^2-X-P-(R^1)_2 \qquad \text{II}$$

wherein $R^2$ is a $C_4$ to $C_{40}$ dideoxycarbohydrate;

each X is independently O or $NR^3$, wherein $R^3$ is H, a $C_1$ to $C_{20}$ alkyl or aryl; and each $R^1$ is an unsubstituted aromatic hydrocarbyl, to yield a chiral, nonracemic mixture of compounds of formula III $$ZZCH-CH(CO_2Z)(NHZ) \qquad \text{III}$$

wherein Z is defined as above;

and wherein in formula II the X groups are attached to $R^2$ in the Left-Right diphosphinite configuration whereby the asymmetric hydrogenation process selectively yields compounds of formula III in R-configuration.

DETAILED DESCRIPTION OF THE INVENTION

The process and catalyst composition of the instant invention whereby enantioselective hydrogenation is accomplished by reacting a dehydroamino acid derivative of the formula $ZZC=C(CO_2Z)(NHZ)$ with hydrogen in the presence of a chiral, nonracemic, metal (Rh, Ir) hydrogenation catalyst, are useful, for example to produce optically active amino acid derivatives. These amino acid derivatives are useful precursors for pharmaceutical products.

The enantioselective hydrogenation reaction is performed by reacting a dehydroamino acid derivative of the formula $ZZC=C(CO_2Z)(NHZ)$ with hydrogen in the presence of a chiral, nonracemic, metal (Rh, Ir) hydrogenation catalyst. These reactions selectively provide optically active D or L -α- amino acid derivatives of the formula $ZZCHCH(CO_2Z)(NHZ)$, where the absolute configuration of the amino acid derivative is determined by the nature of the chiral metal hydrogenation catalyst.

By the term "carbohydrate", Applicants mean the class of organic compounds comprising the general formula $(CH_2O)_n$, wherein n is equal to or greater than four. The carbohydrate-derived ligands of the invention are derived from $C_4$ to $C_{40}$ carbohydrates including monosaccharides, disaccharides and oligosaccharides.

By the term "hydrocarbyl", Applicants include all alkyl, aryl, aralkyl or alkylaryl carbon substituents, either straight-chained, cyclic, or branched, accordingly substituted with hydrogen.

By the term "heterocycle", Applicants mean a cyclic carbon compound containing at least one oxygen, nitrogen or sulfur atom in the ring.

By the term electron-donating group, Applicants include those groups that have σ-values (any σ-values such as $σ_p$, $σ_m$ or their modifications) less than zero (as defined by the Hammett equation, see, for example, March, *J. Advanced Organic Chemistry: Reactions, Mechanisms, and Structure*, 4th ed.; 1992, Wiley: New York, 278–286). Such groups include but are not limited to O–, $NMe_2$, $NH_2$, OH, OMe, $CMe_3$, Me, $Me_3Si$, SMe, and F.

In describing a carbohydrate group of the formula $X-R^2-X$, the "X" can be the same or different and can be O or $NR^3$, where $R^3$ is H, alkyl or aryl; and as it appears within the ligand of the present disclosure, the group $R^2$ is named by using the prefix "dideoxy" with the name of the parent diol of the formula $HO-R^2-OH$. The suffix "pyranose" or "furanose" in combination with the carbohydrate root names shall include those compounds wherein the sugar exists as an internal 6-(pyranose) or 5-(furanose) membered acetal. The OH groups may or may not be protected as esters or ethers. For example, the name "2, 3-dideoxy-glucopyranose" refers to the group:

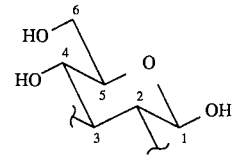

and "3,4-dideoxy-glucopyranose" refers to the group:

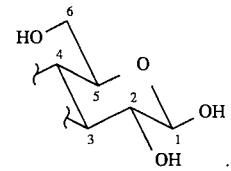

Accordingly, the corresponding carbohydrate groups $O-R^2-O$ are:

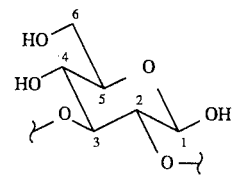

and

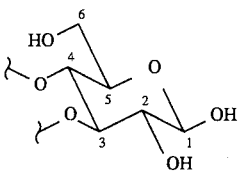

Nitrogen may be substituted for one or both of the oxygens in the above formula $O-R^2-O$ to provide an aminosugar.

An example of the carbohydrate group O—R²—NR³ is the "2,3-dideoxyglucose":

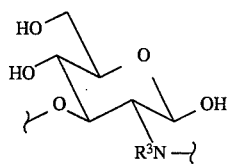

The suffix -ose- when used in combination with carbohydrate root names, shall include those compounds wherein the OH groups are protected as ethers or esters. By this definition, for example, the pyranoside structure shown below is termed a "glucopyranose" since the configuration of the sugar back-bone ($C_1$–$C_5$) is that of the sugar glucose,

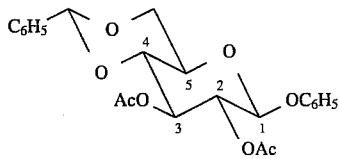

wherein Ac is an acetyl.

By the term "chiral", Applicants mean "existing as a pair of enantiomers." These enantiomers, where the chiral centers are designated the R and S isomers, are nonsuperimposable mirror images of one another. A chiral material may either contain an equal amount of the R and S isomers in which case it is called "racemic" or it may contain inequivalent amounts of R and S isomer in which case it is called "optically active", or "nonracemic". In referring to the amino acid products of the invention, Applicants also use the more familiar "D" and "L" designations to indicate the isomers.

By the term "enantiomeric excess" ("ee"), Applicants mean the absolute difference between the percent of R enantiomer and the percent of S enantiomer of an optically active compound. For example, a compound which contains 75% S isomer and 25% R isomer will have an enantiomeric excess of 50%.

By the terms "enantioselective" or "asymmetric" Applicants mean the ability to produce a product in an optically active form.

The substrates of the invention are the class of dehydroamino acid derivatives. They are described by the formula ZZC=C($CO_2Z$)(NHZ), where each Z is independently H, or a $C_1$ to $C_{20}$ carboalkoxy, $C_1$ to $C_{40}$ aromatic or nonaromatic hydrocarbyl or $C_1$ to $C_{40}$ aromatic or nonaromatic heterocyclic radical; each of which may be substituted with one or more halo, alkoxy, carboalkoxy, nitro, haloalky, hydroxy, amido, keto, or sulfur containing groups. Preferably one of the Z's in the group "ZZC=" is H. Examples of Z include, but are not limited to, phenyl, substituted phenyl, polyaromatic (e.g., napthyl, anthryl), substituted polyaromatic, heteroaromatic, acetoxy, alkyl and substituted alkyl. Representative examples of substrates used in the invention include, but are not limited to, α-acetamidocinnamic acid and its methyl ester; 2-acetamido-3-(4-fluorophenyl)-prop-2-enoic acid and its methyl ester, 2-acetamido-3-(3-methoxyphenyl)prop-2-enoic acid and its methyl ester, methyl 2-acetamido-3-(4-trifluoromethylphenyl)-prop-2-enoate, methyl 2-acetamido-3-(4-methoxyphenyl)-prop-2-enoic acid and its methyl ester, methyl 2-acetamido-3-(4-bromophenyl)-prop-2-enoic acid, methyl 2-N-benzyloxycarbonyl-3-(4-fluorophenyl)-prop-2-enoate, 2-acetamidoacrylic acid, 2-acetamido-3-isopropylacrylic acid, 2-acetamido-3-(2-naphthyl)prop-2-enoic acid and its methyl ester, and methyl 2-acetamido-3-(3-thienyl)prop-2-enoate.

The dehydroamino acid derivatives of the invention may be made by methods which are well-known in the art, e.g., (a) Herbst, R. M.; Shemin, D. in Organic Synthesis, Blatt, A. H. Ed.; John Wiley & Sons Inc., New York; 1943, Coll. Vol II, p 1, (b) U. Schmidt, et al. *Synthesis* 1992, 487, which are hereby incorporated by reference. Several substrates are also available commercially.

For all embodiments of the Applicants' invention, the chiral, nonracemic, metal hydrogenation catalyst composition comprises a chiral, nonracemic, carbohydrate diphosphinite ligand and a source of one or more of the metals Rh and Ir. Suitable sources of the rhodium and iridium include, but are not limited to, the metal halides, olefin complexes, acetoacetates, and carbonyls. Metal compounds that contain ligands which can be displaced by the chiral carbohydrate phosphorus ligand are a preferred source of the metal. In the case, for example, of rhodium (I) intermediates, (COD)₂RhY species (COD is 1,5-cyclooctadiene) are the precursors of choice, with the counterion Y being tetrafluoroborate ($BF_4$), hexafluoroantimonate ($SbF_6$), or trifluoromethanesulfonate (OTf); although other counterions such as tetraphenylborate ($BPh_4$), $PF_6$ and perchlorate ($ClO_4$) would also be suitable. Chiral iridium compounds can be prepared similarly from (COD)₂IrY or (COD)Ir($CH_3CN$)₂Y. Rhodium is the preferred metal.

The catalyst composition also employs a ligand comprising a chiral, nonracemic diphosphinite of the formula ($R^1$)₂—P—X—$R^2$—X—P—($R^1$)₂, wherein the $R^2$ is a $C_4$ to $C_{40}$ dideoxycarbohydrate, optionally substituted with one or more hydrocarbyl, halo, alkoxy, carboalkoxy, hydroxy, amido or keto groups; and such that the fragment of the ligand defined by the structure PX—$R^2$—XP is chiral. In this embodiment X can be the same or different and can be O or $NR^3$ where $R^3$ is H, alkyl or aryl. By this definition Applicants intend that the chirality of the diphosphinite ligand arises from the chirality of the parent carbohydrate diol HO—$R^2$—OH.

Specifically, the process is carried out by employing chiral, nonracemic, O-substituted carbohydrate phosphorus ligands; including particularly pyranose, furanose, disaccharide and oligosaccharide organophosphorus ligands. Examples are represented by the formulas 1–4:

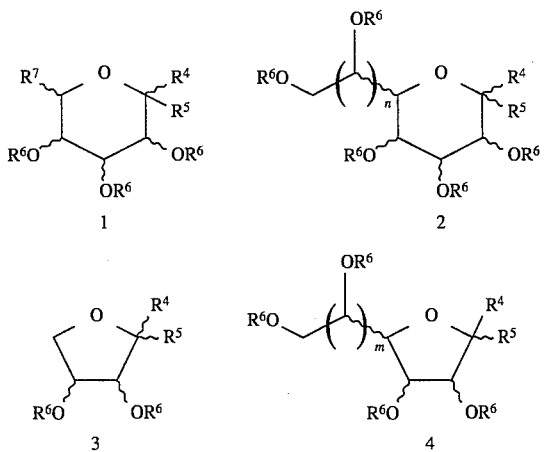

wherein:

n=0–2;

m=0–3;

$R^4$ groups are independently H, $C_1$ to $C_{20}$ hydrocarbyl, alkoxy, aryloxy, O-substituted pyranose or O-substituted furanose;

$R^5$ groups are independently H, hydroxymethyl ($CH_2OH$), alkoxymethyl, aryloxymethyl, or $CH_2OP(R^1)_2$ where $R^1$ is aryl, alkoxy, or aryloxy;

$R^6$ groups are independently H, $C_1$ to $C_{20}$ hydrocarbyl, acyl, or $P(R^1)_2$ where $R^1$ is aryl, alkoxy, or aryloxy;

$R^7$ is H, aryloxy, alkyl, alkoxy, aryloxyalkyl or alkoxyalkyl and the sum total of $P(R^1)_2$ groups present in the X-substituted pyranose, furanose, dissacharide or oligosaccharide organophosphorus ligand is preferably equal to 2.

Examples of $R^2$ include, but are not limited to 2,3-dideoxyglucose, 3,4-dideoxyglucose, 3,4-dideoxyfructose, 3,4-dideoxymannose. By analogy pyranose and furanose forms (whenever applicable) of the following sugars are also possible: 2,3-dideoxyxylose, 2,3-dideoxyxylose, 3,4-dideoxyxylose, 3,4-dideoxyarabinose, 3,4-dideoxysorbose, 2,3-dideoxymaltose, 2',3'-dideoxymaltose, 3',4'-dideoxymaltose, 2,3-dideoxymannose, 2,3-dideoxyallose, 2,3-dideoxylactose, 2'3'-dideoxylactose, 3', 4'-dideoxylactose. The corresponding aminosugar derivatives wherein the oxygen is replaced with acyl or alkyl amino groups are also possible. An example of these derivatives described in this application is:

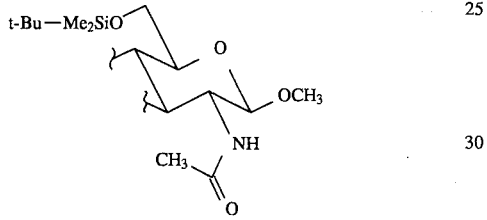

Applicants also specifically include within the carbohydrate ligand compositions of the invention those carbohydrates containing protective groups. By the term "protective group", Applicants include groups such as ethers and esters which function to provide chiral recognition of the sugar molecule, and further are commonly employed to protect the sugar molecule from nonselective reactions. Applicants further intend to particularly include disaccharides formed by joining two of the structures shown in formulas 1–4 through an oxygen atom at the anomeric position of the furanose or pyranose ring. Two examples of such dissacharides are shown below, wherein Ph is phenyl and Ac is acetyl.

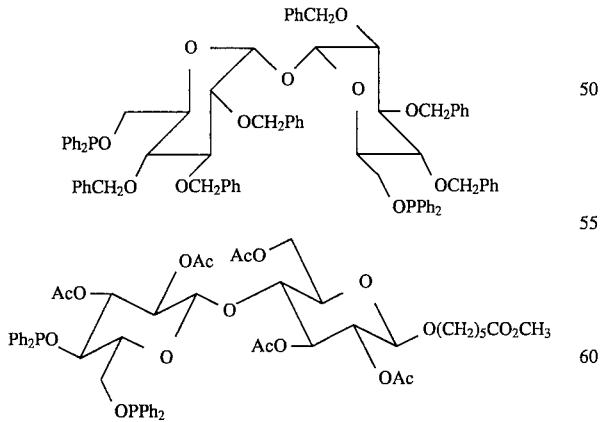

Most preferably, the chiral, nonracemic, organophosphorus ligand is a chiral, nonracemic, O-substituted glucopyranose organophosphorus ligand of the formula 5,

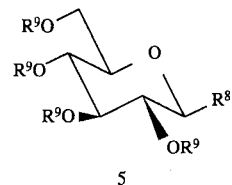

wherein:

$R^8$ is H, $C_1$ to $C_{20}$ hydrocarbyl, alkoxy, or aryloxy;

$R^9$ is independently selected from H, $C_1$ to $C_{20}$ hydrocarbyl, acyl or $P(R^1)_2$, where $R^1$ is aryl, alkoxy, aryloxy;

and the sum total of $P(R^1)_2$ groups present in the O-substituted glucopyranose organophosphorus ligand is equal to 2.

Examples of the ligands used in the present invention include the following:

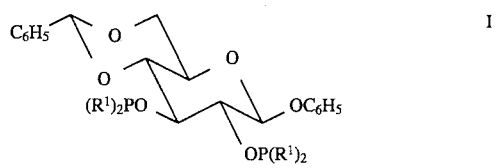

I

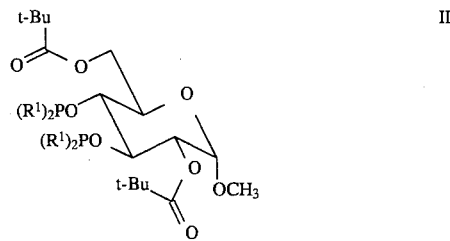

II

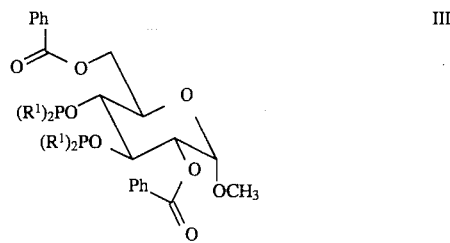

III

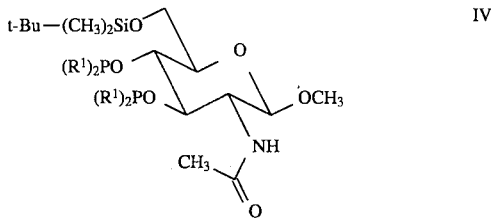

IV

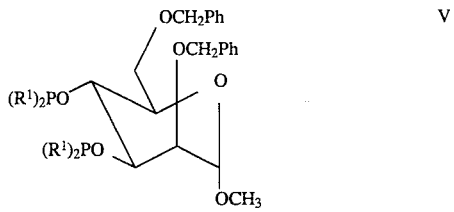

V

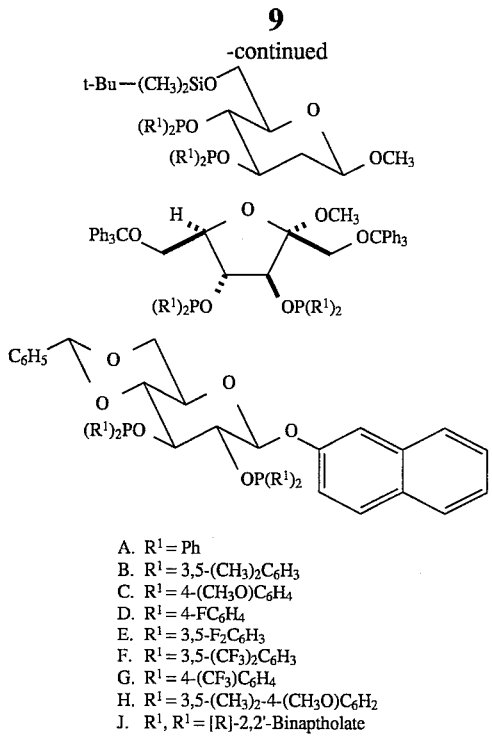

A. $R^1 = Ph$
B. $R^1 = 3,5\text{-}(CH_3)_2C_6H_3$
C. $R^1 = 4\text{-}(CH_3O)C_6H_4$
D. $R^1 = 4\text{-}FC_6H_4$
E. $R^1 = 3,5\text{-}F_2C_6H_3$
F. $R^1 = 3,5\text{-}(CF_3)_2C_6H_3$
G. $R^1 = 4\text{-}(CF_3)C_6H_4$
H. $R^1 = 3,5\text{-}(CH_3)_2\text{-}4\text{-}(CH_3O)C_6H_2$
J. $R^1, R^1 = [R]\text{-}2,2'\text{-Binaptholate}$ Using the above representation of the ligands, the catalysts are described as follows: $[IA]Rh(COD)SbF_6$ refers to a catalyst prepared from ligand IA and $Rh(COD)_2SbF_6$; $[IIB]Rh(COD)BF_4$ refers to a catalyst prepared from ligand IIB and $Rh(COD)_2BF_4$, etc.

For illustrative purpose, ligands IA, IB, IE and IF may be defined as follows in the context of the general definition (i.e., $(R^1)_2\text{—}P\text{—}X\text{—}R^2\text{—}X\text{—}P\text{—}(R^1)_2$) of the:

IA: $R^2$: "2,3-dideoxyglucopyranose" X=O, X=O; $R^1$=Phenyl

IB: $R^2$: "2,3-dideoxyglucopyranose" X=O, X=O; $R^1$=3,5-dimethylphenyl

IE: $R^2$: "2,3-dideoxyglucopyranose" X=O, X=O; $R^1$=3,5-difluorophenyl

IF: $R^2$: "2,3-dideoxyglucopyranose" X=O, X=O; $R^1$=3,5-bis(CF$_3$)phenyl

The ligands of the invention are defined to contain $R^1$ groups which are substituted with electron-donating groups. The beneficial electronic effect of these ligands can be illustrated by comparing ligands IA, IB, IE and IF in the Rh(+)-catalyzed hydrogenation of methyl 2-acetamido-3-(4-fluorophenyl)propen-2-oate. An 85% ee was obtained when diphenylphosphinite IA was used, whereas a 96% ee was obtained with the more electron rich 3,5-dimethylphenyl phosphinite IB. Very low ee's of 13% and 9% were obtained using electron-deficient systems, 3,5-difluorophenylphosphinite IE and 3,5-bis-trifluoromethylphenyl-phosphinite IF, respectively. Applicants believe that utilization of this electronic effect will prove to be highly significant and beneficial in applications necessitating practical means of synthesis of amino acids in very high enantioselectivity.

Examples where high ee's were obtained for the Rh(+)-catalyzed hydrogenation of methyl 2-acetamidocinnamate include IB (S-99.0%), IIB (R-93.0%), IIIB (R-97.0%), and IVB (R-98.3%). The hydrogenation of other substrates are illustrated in the tables.

Another highly significant aspect of the present invention relates to Applicants' recognition that the relative regiochemistry of the vicinal-phosphinites with respect to their location on a given sugar back-bone ("glucose", for example) dictates which amino acid (R or S; or D or L) is generated in the hydrogenation. For example, S-amino acids are obtained when ligands I and VIII are used, whereas R-amino acids are obtained when ligands II, III or IV are used in the reduction of dehydroamino acid derivatives. For purposes of clarity and uniformity, Applicants have characterized and described this element of the invention in terms of the ordered absolute configurations of the phosphinites on sugar back-bone Fisher Projections. In this context, the ordered absolute configuration of the phosphinites on the sugar will be designated unambiguously as either Right-Left, or Left-Right. Applicants are the first to recognize that a Right-Left (occupying the 2,3-position of the sugar) ligand configuration results in formation of the S enantiomer or L amino acid, whereas the Left-Right ligand configuration (occupying the 3,4-position of the sugar) results in formation of the R enantiomer or D amino acid. More specifically, using Fisher Projections (see, for example, Stryer, L. Biochemistry, 3rd ed.; 1988, Freeman: New York, 332–336) of furanose and pyranose derived vicinal diphosphinites, the sense of chirality of products formed in the Rh-catalyzed hydrogenation of dehydroamino acid derivatives can be predicted. In doing so the configuration of the carbon with the lower number is indicated first. Thus, Right-Left diphosphinite indicates that the carbon carrying the right phosphinite is lower in number in the context of the Fisher Projection.

Pyranose and furanose sugars that have a Right-Left diphosphinite configuration (see text for convention) give L-amino acid derivatives (corresponding to S configurations) and those sugars with a Left-Right diphosphinite configuration give D-amino acid derivatives (corresponding to R configurations) when used in the Rh or Ir catalyzed hydrogenation of dehydro-amino acid derivatives.

When the diphosphinites are on the 2,3-positions of D-glucose as shown, the product of the hydrogenation is a L-amino acid (S-configuration). Using Fisher Projections of the sugar derivatives, one can pictorially define the relative location of the diphosphinites on either the left or right side. In this way, by using the standard numbering for carbohydrate nomenclature, the first phosphinite (on the 2-position) is on the right side and the second phosphinite (on the 3-position) is on the left side of the glucose systems. We are defining this as a Right-Left diphosphinite.

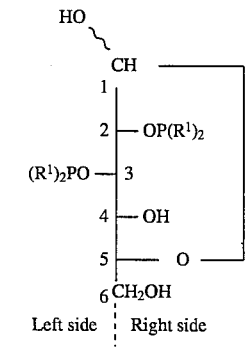

Right-Left diphosphinite from D-Glucose

Accordingly, when diphosphinites are on the 3,4-positions of D-glucose as shown, the product of the hydrogenation is a D-amino acid (R-configuration). Once again using the standard numbering for carbohydrate nomenclature, the first phosphinite (on the 3-position) is on the left side and the second phosphinite (on the 4-position) is on the right side of the glucose systems. We are defining this as a Left-Right diphosphinite.

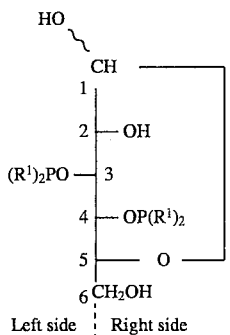

Left-Right diphosphinite from D-Glucose

Correspondingly, other sugar derivatives where a Right-Left diphosphinite is present will provide L-amino acids, whereas a Left-Right diphosphinite will provide D-amino acids when these ligands are used in the hydrogenation of dehydroamino acid derivatives.

Other examples enable us to further illustrate the understanding of this relationship of the sugar diphosphinites to the configuration of the product amino acid derivatives. The 3,4-diphosphinite derived from D-mannose and the 3,4-diphosphinite derived from D-fructose, both Left-Right diphosphinites provide D-amino acid derivatives under the hydrogenation conditions.

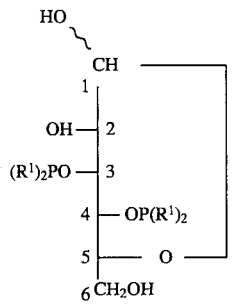

Left-Right diphosphinite from D-Mannose

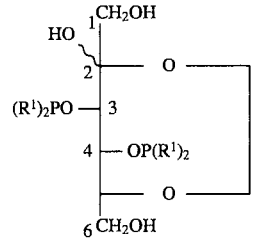

Left-Right diphosphinite from D-Fructose

Also, the 2-deoxy-2-acetamido glucose derivative shown below is a Left-Right diphosphinite and provides D-amino acids under the hydrogenation conditions

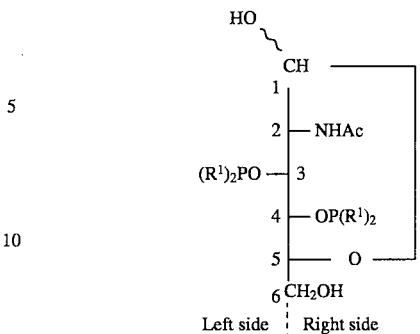

Left-Right diphosphinite from D-Glucose

Within the context of the ligand formula II $(R^1)_2$—P—X—$R^2$—X—P—$(R^1)_2$ and the ligand nomenclature developed above, the ligands IB, IIIB and IVB may be compared in the process of the invention to further illustrate this configurational effect:

IB: $R^2$:"2,3-dideoxyglucopyranose" X=O,X=O; $R^1$=3,5-dimethylphenyl

IIIB: $R^2$: "3,4-dideoxyglucopyranose" X=O,X=O; $R^1$=3,5-dimethylphenyl

IVB: $R^2$: "3,4-dideoxyglucopyranose" X=O,X=O; $R^1$=3,5-dimethylphenyl

When $R^1$=bis-(2,3-dimethylphenyl)phosphino, ligand IB serves as an efficient ligand for Rh(+) in the catalytic hydrogenation of methyl acetamidocinnamate which is reduced to the corresponding S(+) methyl phenylalaninate in 99.0% ee. Under identical conditions, 93.0 and 98.3% ee of the R(−) isomer are obtained using ligand IIIB and IVB, respectively.

The configurationally specific chiral, nonracemic carbohydrate-derived diphosphorus ligands can be prepared according to techniques well-known in the art. (Selke, R.; Facklam, C.; Foken, H.; Heller, D. *Tetrahedron Asymmetry* 1993, 4, 369; Baker, M. J.; Pringle, P. G.; *J. Chem. Soc. Commun.* 1991, 1292; Habus, I.; Raza, Z; Sunjic, V. *J. Mol. Catal.* 1987, 42, 173.; Jackson, W. R.; Lovel, C. G. *Aust. J. Chem.* 1982, 35, 2069; Jackson, R.; Thompson, D. J. *J. Organomet. Chem.* 1978, 159, C29; Cullen, W. R.; Sugi, Y.; *Tetrahedron Lett.* 1978, 1635). In general, diol derivatives containing unprotected hydroxyl groups are treated with a $P(R)_2Cl$ (wherein R may generally be an alkyl, aryl, alkoxy, or aryloxy) reagent, in the presence of a base, such as pyridine or triethylamine, to produce the desired phosphinite or phosphite. Some $P(R)_2Cl$ reagents are commercially available, such as $PPh_2Cl$ (Ph=phenyl). Other $P(R)_2Cl$ reagents, where R=aryl or alkyl, can be prepared by two methods. Method A involves the reaction of (amino) dichlorophosphines such as $Et_2NPCl_2$ with RMgBr followed by reaction with HCl [Methoden Der Organischen Chemie (Houben-Weyl): Vol 12, Part 1; Muller, E., ed.; Georg Theme Verlag: Stuggart, 1963, 213–215; de Koe, P.; Bickelhaupt, F. *Angew. Chem. Int. Ed., Eng.* 1967, 6, 567; Quin, L. D.; Anderson, H. G. *J. Org. Chem.* 1966, 31, 1206.; Montgomery, R. E.; Quin, L. D. *J. Org. Chem.* 1965, 30, 2393; Frank, A. *J. Org. Chem.* 1961, 26, 850].Alternatively, treatment of readily available dialkyl phosphites, such as dibutyl phosphite, $HP(O)(OBu)_2$, with RMgBr followed by reaction with $PCl_3$ provides $P(R)_2Cl$ derivatives (U.S. Pat. No. 5,175,335). $P(R)_2Cl$ reagents, where R=alkoxy or aryloxy, can be prepared in two steps by treatment of $P(NEt_2)_3$ ROH to generate $P(OR)_2(NEt_2)$, followed by treatment with $CH_3COCl$ to generate $P(OR)_2Cl$. Illustrative preparations are provided below.

For all embodiments of the invention the chiral, nonracemic metal hydrogenation catalyst may be prepared by mixing the metal source and the chiral, nonracemic, organophosphorus ligand, preferably in a suitable organic solvent under an inert atmosphere such as $N_2$ or Ar in a temperature range from 0° C. to 120° C., preferably in a temperature range from 0° C. to 80° C. The metal compound may be used in this solution or the metal compound can be obtained in the pure form upon removal of the solvent. Rh is the preferred metal. Counter ions $BF_4$ and $SBF_6$ are preferred.

The preferred molar ratio of chiral, nonracemic, organophosphorus ligand to the metal may vary between 1:1 to 2:1, most preferably between 1:1 to 1.2:1.

The preferred molar ratio of metal complex to vinyl compound may vary between 0.00005:1 to 1:1, most preferably between 0.0001:1 to 0.01:1.

The dehydroamino acid derivative, represented by the formula $ZZC=C(CO_2Z)(NHZ)$ may be dissolved in any organic solvent such as, but not limited to, tetrahydrofuran, methanol, ethanol, dimethoxyethane, toluene or hexane. Tetrahydrofuran (THF), methanol, ethanol and dimethoxyethane and mixtures thereof are preferred solvents. THF is the most preferred.

The hydrogen can be provided by contacting the reaction mixture with hydrogen gas.

The hydrogenation reaction is preferably conducted over a temperature range from −25° C. to 100° C., most preferably 25° to 30° C. Applicants note that higher ee's are observed at lower temperatures. Suitable pressure range is 10–100 psi (1 psi=6.9 kPa).

The enantioselective hydrogenation reactions are typically complete within 3–24 hours.

To demonstrate a preferred mode of the invention which produces a particularly useful product, preparation of optically active (R)-(+)-phenylalanine can be achieved. The catalyst composition comprises a cationic rhodium (I) compound and the ligand formula $(R^1)_2P—X—R^2—XP(R^1)_2$ wherein each $R^1$ is the aryl group 3,5-dimethylphenyl and $R^2$ is the O-substituted β-D-glucopyranose of the formula IIIB, the starting acrylate derivative is α-acetamidocinnamic acid, and the source of rhodium metal is $(COD)_2RhSbF_6$.

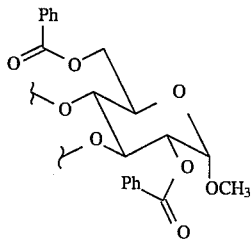

IIIB

For the preparation of (R)-(+)-phenylalanine, the enantioselective hydrogenation is preferably carried out at 25° C. under 40 psi pressure of hydrogen. A mixture of α-acetamidocinnamic acid and the chiral rhodium catalyst is stirred in a suitable solvent such as THF, DME, or $CH_3OH$ for 3 h. In this preferred embodiment, a molar ratio between 0.0025:1 to 0.05:1 of rhodium catalyst to acrylate derivative is used.

Using these preferred conditions, ee's greater than 95% are typically obtained. Isolation of the product amino acid in 90–100% yield can be achieved by crystallization from the reaction mixture.

General Procedures for the Preparation of Chiral Carbohydrate Diols, Phosphinite Ligands $(R^1)_2P—X—R_2—X—P(R^1)2$ and Rh and Ir Catalysts Derived Therefrom A. Synthesis of Diols The requisite diols for the ligand synthesis (see Table 1) were prepared by procedures outlined below.

Phenyl 4,6-O-benzylidene-β-D-glucopyranoside. The title compound was prepared by treatment of commercially available phenyl-β-D-glucopyranoside with dimethoxytoluene in the presence of p-toluenesulfonic acid in acetonitrile (for leading references see Carbohydrates, Ed. Collins, P. M., Chapman and Hall, New York, 1987, 414).

Methyl 2,6-di-O-pivaloyl-α-D-glucopyranoside and Methyl 2,6-di-O-benzoyl-α-D-glucopyranoside. The requisite carbohydrate diols were synthesized according to literature procedures: (Ogawa, T.; Matsui, M. Tetrahedron 1981, 37, 2369; Tomic-Kulenovic, S.; Keglevic, D. Carbohydrate Res. 1980, 85, 302.).

Methyl 2-acetamido-2-deoxy-6-O-t-butyldimethylsilyl-β-D-glucopyranoside. This compound was prepared from the corresponding methyl glucoside, Methyl 2-acetamido-2-deoxy-β-D-glucopyranoside (Carbohydrates, Ed. Collins, P. M., Chapman and Hall, New York, 1987, p. 414) by treatment with t-butyldimethychlorosilane in DMF and imidazole. $^1H$ NMR δ0.00 (2×s, 6H), 0.80 (2×s, 9H), 1.98 (s, br, 3H), 3.20–3.32 (m, 1H), 3.32–3.50 (s superimposed on m 5H), 3.59 (dd, J=12, 8, 1H), 3.76, 3.84 (ABX, JAB=18, 2H), 4.28 (d, J=8, 1H), 6.42 (d br J=4, 3H).

Methyl 2-deoxy-6-O-t-butyldimethyl-α-D-glucopyranoside. This compound was prepared from the corresponding methyl glucoside, Methyl 2-deoxy-α-D-glucopyranoside. (Carbohydrates, Ed. Collins, P. M., Chapman and Hall, New York, 1987. p. 352) by treatment with t-butyldimethylchlorosilane in DMF and imidazole. $^1H$ NMR δ4.73 (d, 1, J=3 Hz), 3.85–3.78 (M, 4), 3.55–3.46 (m, 2), 3.35 (m, 1), 3.29 (s, 3), 2.05 (m, 1), 1.61 (m, 1), 0.88 (m, 9), 0.07 (m, 6).

Methyl 2,6-di-O-benzyl-α-D-mannopyranoside. A ca. 2:1 mixture of exo-and endo-isomers of bis-[(2,3-O-), (4,6-O-)] benzylidene-α-D-mannopyranoside (Carbohydrates, Ed. Collins, P. M., Chapman and Hall, New York, 1987, p. 350) was prepared by reaction of methyl α-D-mannopyranoside with 2.2 eq of α,α-dimethoxytoluene and catalytic p-toluenesulfonic acid in acetonitrile. This compound was treated with $NaBH_4$ and HCl (Garegg, P. J.; Hultberg, H. Carbohydrate Res. 1981, 93, C10) to provide a mixture of products from which the methyl 2,6-O-benzyl-α-D-mannopyranoside was isolated by flash chromatography. The assignment of this isomer was confirmed by $^1H$ decoupling experiments on the corresponding bis-(3,4-O-diphenylphosphino) derivative (ligand VA). $^1H$ NMR δ7.42–7.24 (m, 10), 4.81 (d, 1, J=1 Hz), 4.75–4.54 (m, 4), 3.78–3.71 (m, 6), 3.36 (s, 3), 2.83 (s, 1), 2.43 (bs, 1).

Methyl 1,6-O-trityl-α-D-fructofuranoside. The starting diol was prepared by tritylation of Methyl-α-D-fructofuranoside. Carbohydrates, Ed. Collins, P. M., Chapman and Hall, New York, 1987, 356) with trityl chloride in pyridine.

B. Example of Modified Procedure for the Synthesis of $Ar_2PCl$

Di-[(3,5-bis-trifluoromethyl)-phenyl]chlorophosphine. A 1.0M solution of (3,5-bis-trifluoromethyl)phenylmagnesium bromide was prepared by slow addition of 18.5 g (60 mmol) of (3,5-bis-trifluoromethyl)bromobenzene in 40 mL of THF to a slurry of Mg turnings in 20 mL of THF. After 1 h, this solution was added slowly to a solution of 5.0 g (29 mmol) of $Et_2NPCl_2$ in 30 mL of THF at 0° C. After 2 h, the mixture was concentrated in vacuo. Cyclohexane (100 mL) was added and the mixture was filtered through celite to provide a solution of [di-3,5-bis(trifluoromethyl)phenyl](diethylamino)phosphine. Dry HCl was passed through this solution for 1 h. After filtration under a nitrogen atmosphere (in some instances, it was necessary to degas the solution to precipitate the amine hydrochloride) and concentration, 12.4 g (88%) of 1a was collected as a white solid. $^{31}P$ NMR δ69.8; $^1H$ NMR δ7.66 (m, 4) 7.52 (s, 2).

Bis-(4-methoxyphenyl)chlorophosphine. $^{31}P$ NMR δ85.4; $^1H$ NMR δ7.54 (m, 4), 6.65 (m, 4), 3.17 (s, 6), $^{13}C$ δ134.0 (d, 1, $J_{PC}$=26 Hz), 128.4 (d, 1, $J_{PC}$=24 Hz), 128.2 (d, 1, $J_{PC}$=24 Hz), 114.6 (d, 1, $J_{PC}$=8 Hz), 54.8.

Bis-(3,5-dimethylphenyl)chlorophosphine. $^{31}P$ NMR d 85.3; $^1H$ NMR d 7.25 (m, 4), 6.62 (s, 2), 1.85 (m, 12).

Bis-(3,5-difluorophenyl)chlorophosphine. $^{31}P$ NMR δ75.3; $^1H$ NMR δ6.93 (m, 4), 6.43 (m, 2).

Bis-(3,5-dimethyl-4-methoxyphenyl)chlorophosphine. $^{31}P$ NMR δ89.2; $^1H$ NMR δ7.42 (d, 4, J=12 Hz), 3.18 (s, 6), 1.98 (s, 12).

Bis-(4-fluorophenyl)chlorophosphine. $^{31}P$ NMR δ80.6; $^1H$ NMR δ7.12 (m, 4), 6.58 (m, 4).

Bis-(4-trifluoromethylphenyl)chlorophosphine. $^{31}P$ NMR δ76.3; $^1H$ NMR δ7.33 (m, 8).

C. Synthesis of Phosphinites

The ligands were synthesized according to methods previously reported in U.S. Pat. No. 5,175,335 (Casalnuovo, A.L.;RajanBabu, T. V.) and the reference, Selke, R.; Pracejus, H. *J. Mol. Catal.* 1986, 37, 213.

D. Synthesis of Metal Catalysts

In a dry box under nitrogen, a solution of 0.49 mmols of $Rh(COD)_2^+X^-$ (X=$SbF_6$,$BF_4$,$OSO_2CF_3$) in 5 mL of $CH_2Cl_2$ was added to 0.05 mmol of phosphinite in 5 mL of $CH_2Cl_2$ at room temperature. The mixture was stirred for 30 min to 3 h and the solvent was carefully removed under vacuum. A fine powder of the Rh-complex may be obtained by redissolving the complex in 8 mL of benzene and freeze-drying the sample under high vacuum.

The following ligands and the corresponding catalysts were prepared according to general procedures (A-D) outlined earlier and the structures were confirmed by $^1H$ NMR and $^{31}P$ NMR.

I. Ligands and catalysts from phenyl 4,6O-benzylidene-β-D-glucopyranoside

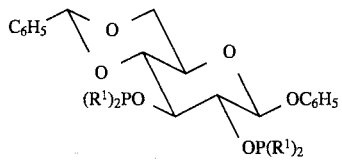

IA. (2,3-diphenylphosphinite), $R^1$=Ph (see U.S. Pat. No. 5,175,335, and Selke, R.; Pracejus, H. *J. Mol. Catal.* 1986, 37, 213 for ligand synthesis): [IA]Rh(COD)SbF$_6$ $^{31}P$ NMR(CDCl$_3$): ABX (=P$_1$P$_2$Rh), $n_a$=137.5, $n_b$=138.6, $J_{AB}$=27 Hz, $J_{AX}$=$J_{BX}$(=$J_{RhP}$)=176 Hz; [IA]Rh(COD)BF$_4$ $^{31}P$ NMR: ABX (=P$_1$P$_2$Rh), $\eta_A$=136.5, $\eta_B$=138.0, JAB=27 Hz, JAX=JBX (=$J_{RhP}$)=178 Hz.

Iridium Catalyst [IA]Ir(COD)BF$_4$ $^{31}P$ NMR: 118.6 (d, 1, $J_{pp}$=28 Hz), 120.0 (d, 1, $J_{pp}$=28 Hz).

IB. (Di-(bis-3,5-dimethylphenyl)phosphinite), $R^1$=3,5-$(CH_3)_2C_6H_3$ (for ligand see: U.S. Pat. No. 5,175,335):

[IB]Rh(COD)SbF$_6$ $^{31}P$ NMR(CDCl$_3$): ABX (=P$_1$P$_2$Rh), $n_a$=136.6, $n_b$=136.8, $J_{AB}$=27 Hz, $J_{AX}$=$J_{BX}$ (=$J_{RhP}$)=177 Hz; in C$_6$D$_6$ ABX (=P$_1$P$_2$Rh), $\eta_A$=134.0, $\eta_B$=136.0, $J_{AB}$=29 Hz, $J_{AX}$=$J_{BX}$ (=$J_{RhP}$)=178 Hz.

IC. (Di-(4-methoxyphenyl)phosphinite), $R^1$=4-MeO-$C_6H_4$: IC. $^1H$ NMR 3.12 (s, 3H), 3.17 (s, 3H), 3.18 (s, 3H), 3.20 (s, 3H), 3.29 (t, J=10, 1H), 3.54 (t, 10, 1H), 3.92 (dd, J=10, 4, 1H), (4.51–4.55 (2 X dd, 2H), 4.58 (s, 1H), 4.59 (d, J=8 Hz), 6.50–7.60 (m, aromatic); $^{31}P$ 116.59 (d, J=3, 1 P), 121.06 (d, J=3, 1 P). [IC]Rh(COD)SbF$_6$ $^{31}P$ NMR (C$_6$D$_6$) ABX (=P$_1$P$_2$Rh), $n_a$=139.5, $n_b$=140.1, $J_{AB}$=24 Hz, $J_{AX}$=$J_{BX}$ (=$J_{RhP}$)=182 Hz; [IC]Rh(COD)OTf $^{31}P$ NMR (C$_6$D$_6$) ABX (=P$_1$P$_2$Rh), $\eta_A$=136.8, $\eta_B$=138.5, $J_{AB}$=28 Hz, $J_{AX}$=$J_{BX}$ (=$J_{RhP}$)=181 Hz.

ID. (Di-(4-fluorophenyl)phosphinite), $R^1$=4-F-$C_6H_4$: $^1H$ NMR δ7.35–6.40 (m, 26), 4.82 (d, 1, J=8 Hz), 4.42 (m, 2), 3.91 (dd, 1 J=5, 10 Hz), 3.28 (m, 2), 3.11 (m, 1); $^{31}P$ NMR δ118.0, 114.8. [ID]Rh(COD)SbF$_6$ $^{31}P$ NMR(CDCl$_3$): multiplet superimposed on an ABX 8-line pattern with further small coupling presumably due to long range interaction with fluorines. d126.5, 126.8, 128.0, 128.3, 129.2, 129.5, 130.8, 131.1.

IE. (Di-(3,5-difluorophenyl)phosphinite), $R^1$=3,5-$F_2C_6H_3$ (for ligand, see U.S. Pat. No. 5,175,335). [IE]Rh(COD)SbF$_6$ $^{31}P$ NMR(CDCl$_3$): ABX (=P$_1$P$_2$Rh), $\eta_A$=134.7, $\eta_B$=137.9, $J_{AB}$=28 Hz, $J_{AX}$=$J_{BX}$ (=$J_{RhP}$)=182 Hz.

IF. (Di-(bis-3,5-trifluoromethylphenyl)phosphinite), $R^1$=3,5-$(CF_3)_2C_6H_3$ (for ligand, see U.S. Pat. No. 5,175,335. [IF]Rh(COD)SbF$_6$ $^{31}P$ NMR(C$_6$D$_6$): ABX (=P$_1$P$_2$Rh), $\eta_A$=126.8, $\eta_B$=130.5, $J_{AB}$=36 Hz, $J_{AX}$=$J_{BX}$ (=$J_{RhP}$)=182 Hz.

IG. (Di-(4-trifluoromethylphenyl)phosphinite), $R^1$=4-$CF_3C_6H_4$: $^1H$ NMR (C$_6$D$_6$) 3.05(m, 1H), 3.10–3.20 (m, 2H), 3.90 (dd, J=10,6,1H), 4.36 (m, 2H), 4.71 (s, 1H), 4.78 (d, J=7 Hz, 1H), 6.28 (d, J=7 Hz, 1H), 6.66–7.40 (m, aromatic); $^{31}P$ 113.0, 115.7; [IG]Rh(COD)BF$_4$ $^{31}P$ NMR(C$_6$D$_6$): 125.0 (JPP=36, 1 P), 117.3 ($J_{PP}$=36 Hz, 1 P), $J_{RhP}$=173 Hz.

IJ. (([R]-2,2'-O-Binapthyl)phosphinite), $R_1$,

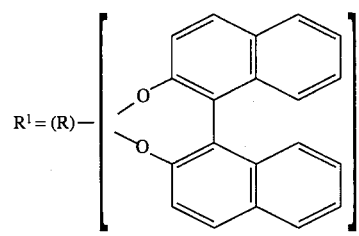

(for ligand, see U.S. Pat. No 5,175,335) [IJ]Rh(COD)BF$_4$ $^{31}P$ NMR(C$_6$D$_6$): ABX (=P$_1$P$_2$Rh), $\eta_A$=132.7, $\eta_B$=138.7$J_{AB}$=(=$J_{PP}$)=55 Hz, $J_{AX}$=$J_{BX}$ (=$J_{RhP}$)=255 Hz.

Ligands and catalysts from Methyl-2,6-O-bis-(trimethylacetyl)-α-D-glucopyranoside

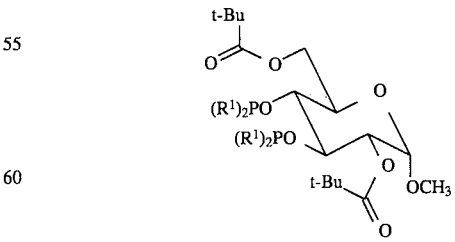

IIA. (3,4-diphenylphosphinite), $R^1$=Ph: $^1H$ NMR δ7.50–6.78 (m, 20), 5.25 (dd, 1, =4, 10 Hz), 5.05 (m, 1), 5.00 (d, 1, J=3 Hz), 4.44 (m, 1), 4.17 (dd, 1, J=2, 12 Hz), 3.94 (ddd, 1, J=2, 5, 10 Hz), 3.75 (dd, 1, J=5, 12 Hz), 2.97 (s, 3), 1.14 (s, 9) 0.93 (s, 9): $^{31}$P NMR δ118.0 (d, 1, $J_{pp}$=5 Hz), 114.8 (d, 1, $J_{pp}$=5 Hz); [IIA]Rh(COD)BF$_4$ $^{31}$P NMR(C$_6$D$_6$): ABX (=P$_1$P$_2$Rh), $\eta_A$=134.0, $\eta_B$=136.5, $J_{AB}$=30 Hz, $J_{AX}$=$J_{BX}$ (=$J_{RhP}$)=178 Hz.

IIB. (3,4-Di-(bis-3,5-dimethylphenyl)phosphinite), R$^1$=3,5-(CH$_3$)$_2$C$_6$H$_3$: $^1$H NMR δ7.35–7.18 (m, 6), 6.95–6.85 (m, 2), 6.64 (s, 1), 6.53 (s, 1), 6.47 (s, 1), 6.33 (s, 1), 5.30 (m, 1), 5.08 (m, 1), 4.89 (m, 1), 4.50 (m, 1), 4.12 (dm, 1, J=12 Hz), 3.95 (m, 1), 2.88 (s, 3), 1.99 (s, 6), 1.98 (s, 6), 1.93 (s, 6), 1.90 (s, 6); $^{31}$P NMR δ122.1, 117.9; [IIB]Rh(COD)BF$_4$ $^{31}$P NMR(C$_6$D$_6$): ABX (=P$_1$P$_2$Rh), $\eta_A$=129.0, $\eta_B$=135.2, $J_{AB}$=30 Hz, $J_{AX}$=$J_{BX}$ (=$J_{RhP}$)=176.

IIF. (3,4-Di-(bis-3,5-trifluoromethylphenyl)phosphinite), R$^1$=3,5-(CF$_3$)$_2$C$_6$H$_3$: $^1$H NMR δ8.01–6.63 (m, 12), 5.02 (dd, 1, J=4, 10 Hz), 4.86 (m, 1), 4.83 (d, 1J=4 Hz). 4.06 (m, 1), 3.86 (m, 2), 3.65 (dd, 1, J=6, 12 Hz), 2.90 (s, 3), 1.01 (s, 9), 0.85 (s, 9); $^{31}$P NMR δ111.9, 105.7.; [IIF]Rh(COD)BF$_4$ In addition to the eight line pattern at 125.3, 125.7, 126.1, 126.4, 127.2, 127.6, 127.9 there is another set of broad doublets which appear around δ130, 132, 141 and 143.

IIH. (3,4-Di-{(bis-3,5-dimethyl)-4-O-methylphenyl}phosphinite), R$^1$=3,5-(CH$_3$)$_2$-4-(CH$_3$O)-C$_6$H$_2$: $^1$H NMR δ7.39 (m, 4), 7.30 (m, 2), 7.09 (m, 2), 5.39 (dd, 1, J=4, 10 Hz), 5.19 (m, 1), 4.97 (d, 1, J=4 Hz), 4.57 (m, 1), 4.12 (dd, 1, J=1, 12 Hz), 4.04 (ddd, 1, 4, 10 Hz), 3.77 (dd, 1, J=5, 12 Hz), 3.38 (m, 3), 3.28 (m, 3), 3.22 (s, 3), 3.14 (s, 3), 2.95 (s, 3), 2.17 (s, 3), 2.12 (s, 6), 2.11 (s, 3), 1.16 (s, 9), 0.96 (s, 9); $^{31}$P NMR δ123.2 (d, 1, $J_{pp}$=3 Hz), 117.8 (d, 1, $J_{pp}$=3 Hz). [IIH]Rh(CODBF$_4$ $^{31}$P NMR(C$_6$D$_6$): ABX (=P$_1$P$_2$Rh), $\eta_A$=129.3, $\eta_B$=135.6$J_{AB}$=30 Hz, $J_{AX}$=$J_{BX}$ (=$J_{RhP}$)=176 Hz.

III. Ligands and catalysts from methyl 2,6-O-dibenzoyl-α-D-glucopyranoside

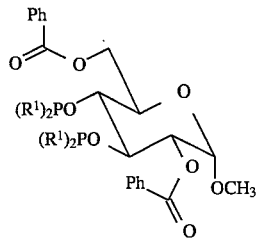

IIA. (3,4-diphenylophosphinite), R$_1$=Ph: $^1$H NMR δ8.12 (m, 2), 7.85 (m, 2), 7.50–6.49 (m, 16), 5.40 (dd, 1, J=4, 12 Hz), 5.22 (m, 1), 5.08 (d, 1, J=3 Hz), 4.70 (m, 1), 4.39 (d, 1, J=12 Hz), 4.04 (dd, 1, J=4, 10 Hz), 3.91 (dd, 1, J=4, 12 Hz), 2.78 (s, 3); $^{31}$P NMR δ120.0 (d, 1, $J_{PP}$=4 Hz), 116.0 (d, 1, $J_{PP}$=4 Hz). [IIA]Rh(CODBF$_4$ NMR (C$_6$D$_6$): ABX (=P$_1$P$_2$Rh), $\eta_A$=130.8, $\eta_B$=133.7, $J_{AB}$=32 Hz, $J_{AX}$=$J_{BX}$ (=$J_{RhP}$)=176 Hz.

IIIB. (3,4-Di-(bis-3,5-dimethylphenyl)phosphinite), R$^1$=3,5-(CH$_3$)$_2$C$_6$H$_3$: $^1$H NMR δ8.13 (m, 2), 7.80 (m, 2), 7.30–6.70 (m, 14), 6.63 (s, 1), 6.46 (s, 1), 6.32 (s, 1), 6.03 (s, 1), 5.51 (dd, 1, J=4, 10 Hz), 5.23 (m, 1), 5.00 (d, 1, J=3 Hz), 4.89 (m, 1), 4.42 (d, 1, J=12 Hz), 4.04 (dd, 1, J=4, 10 Hz), 3.90 (dd, 1, J=4, 12 Hz), 2.75 (s, 3), 2.02 (s, 6), 1.91 (s, 6), 1.88 (s, 6), 1.73 (s, 6); $^{31}$P NMR δ124.7, 118.8. [IIIB]Rh(COD)BF$_4$NMR C$_6$D$_6$): ABX (=P$_1$P$_2$Rh), $\eta_A$=129.0, $\eta_B$=130.4, $J_{AB}$=10 Hz, $J_{AX}$=$J_{BX}$(=$J_{RhP}$)=175 Hz; [IIIA]Rh(COD)SbF$_6$ NMR(C$_6$D$_6$): ABX (=P$_1$P$_2$Rh), $\eta_A$=132.8, $\eta_B$=134.2, $J_{AB}$=30 Hz, $J_{AX}$=$J_{BX}$ (=$J_{RhP}$)=151 Hz.

IIIC. (3,4-Di-(4-methoxyphenyl)phosphinite), R$^1$=4-(CH$_3$O)C$_6$H$_4$: $^1$H NMR δ8.40–6.46 (m, 26), 5.69 (dd, 1, J=4, 10 Hz), 5.45 (m, 1), 5.27 (d, 1, J=4 Hz), 4.93 (m, 1), 4.65 (dd, 1, J=2, 12 Hz), 4.29 (m, 1), 4.19 (m, 1), 3.41 (s, 3), 3.34 (s, 3), 3.32 (s, 3), 3.19 (s, 3), 3.02 (s, 3); $^{31}$P NMR δ120.5 (d, 1, $J_{pp}$=5 Hz), 117.8 (d, 1, $J_{pp}$=5 Hz). [IIIC] Rh(COD)BF4 NMR(C$_6$D$_6$): ABX (=P$_1$P$_2$Rh), $\eta_A$=134.4, $\eta_B$=136.1, $J_{AB}$=28 Hz, $J_{AX}$=$J_{BX}$ (=$J_{RhP}$)=181 Hz.

[IIIE]Rh(COD)BF$_4$ NMR(C$_6$D$_6$): ABX (=P$_1$P$_2$Rh), $\eta_A$=126.7, $\eta_B$=127.6, $J_{AB}$=39 Hz, $J_{AX}$=$J_{BX}$ (=$J_{RhP}$)=179 Hz.

IIIF. (3,4-Di-(bis-3,5-trifluoromethylphenyl)phosphinite, R$^1$=3,5-(CF$_3$)$_2$C$_6$H$_3$: $^1$H NMR δ8.22–6.89 (m, 32), 5.45 (dd, 1, J=4, 10 Hz), 5.19 (m, 1), 5.11 (d, 1, J=4 HZ), 4.52 (m, 1), 4.28 (d, 1, J=12 Hz), 4.11 (dd, 1, J=5, 10 Hz), 3.98 (dd, 1, J=5 12 Hz), 2.93 (s, 3); $^{31}$P NMR δ113.0, 107.5.

IIIG. (3,4-Di-(4-trifluoromethylphenyl)phosphinite), R$^1$=4-CF$_3$C$_6$H3 $^1$H NMR(C$_6$D$_6$) 2.80 (s, 3H), 3.85 (dd, J=13, 4, 1H), 4.06 (ddm, J=8, 4, 1H), 4.28 (dd, J=13, 2, 1H), 4.60 (dt, J=12, 12 1H), 5.00 (m, 1H), 5.03 (d, J=4, 1H), 5.28 (dd, 12, 4, 1H), 6.70–7.60 (m, aromatic); [IIIG] Rh(COD)BF$_4$ NMR(C$_6$D$_6$): ABX (=P$_1$P$_2$Rh), $\eta_A$=125.2, $\eta_B$=127.4, $J_{AB}$=37 Hz, $J_{AX}$=$J_{BX}$ (=$J_{RhP}$)=177 Hz.

IV. Ligands and catalysts from methyl-2-acetamido-6-O-(t-butyldimethylsilyl)-2-deoxy-β-D-glucopyranoside

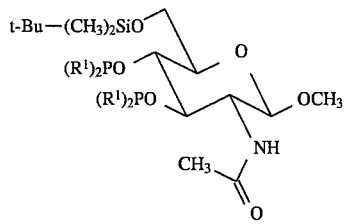

IVA. (3,4-diphenylphosphinite), R$^1$=Ph Ligand: $^{31}$P NMR (C$_6$D$_6$) 112.70 (d, $J_{PP}$=5 Hz), 117.17 (d, $J_{PP}$=5 Hz); [IVA] RhSbF$_6$ (C$_6$D$_6$) ABX (=PPRh), $\eta_A$=122.5, $\eta_B$=129.2, $J_{AB}$ (JPP)=35, $J_{RhP}$=173.

IVB. (3,4-Di-(bis-3,5-dimethylphenyl)phosphinite), R$^1$=3,5-(CH$_3$)$_2$C$_6$H$_3$: $^1$H NMR δ7.55–7.22 (m, 8), 6.86 (s, 1), 6.72 (s, 1), 6.64 (s, 1), 6.59 (s, 1), 5.26 (m, 1), 5.13 (d, 1, J=8 Hz), 4.73 (m, 2), 4.42 (m, 1), 3.80 (m, 3), 3.49 (s, 3), 2.20 (s, 15), 2.17 (s, 6), 2.11 (s, 6), 1.12 (s, 9), 0.16 (s, 3), 0.15 (s, 3); $^{31}$P NMR δ120.4 (d, 1, $J_{pp}$=4 Hz), 115.7 (d, 1, $J_{pp}$=4 Hz); [IVB]RhBF$_4$ (C$_6$D$_6$) ABX (=PPRh), $\eta_A$=118.9, $\eta_B$=126.6, $J_{AB}$ (JPP)=34, $J_{RhP}$=170.

V. Ligands and catalysts from methyl-2,6-O-dibenzyl-α-D-mannopyranoside

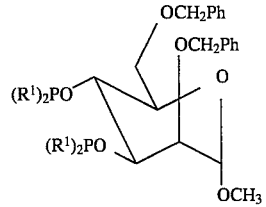

VA. (3,4-diphenylphosphinite), R$^1$=Ph: $^1$H NMR δ7.78–6.80 (m, 20), 5.09 (m, 1), 4.95 (m, 1), 4.72 (d, 1, J=2, Hz), 4.22 (m, 4), 4.11 (m, 1), 4.02 (m, 1), 3.55 (m, 2), 3.13 (s, 3); $^{31}$P NMR δ117.3, 110.4; [VA]Rh(COD)BF$_4$ (C$_6$D$_6$) $^{31}$P: $\eta_A$=129.2, $\eta_B$=137.2, $J_{PP}$=27, $J_{RhP}$=177; [VB] Rh(COD)BF$_4$(C$_6$D$_6$) $^{31}$P: $\eta_A$=124.8, $\eta_B$=133.9, $J_{pp}$=30; $J_{Rh,P}$=176.

VI. Ligands and catalysts from methyl-6-O-(t-butyldimethylsilyl)-2-deoxy-α-D-glucopyranoside

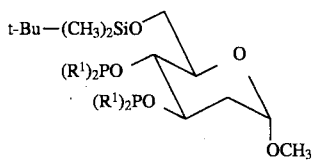

VIB. (3,4-Di-(bis-3,5-dimethylphenyl)phosphinite), $R^1$=3,5-$(CH_3)_2C_6H_3$: $^1H$ NMR δ7.61–7.26 (m, 8), 6.88 (s, 1), 6.81 (s, 1), 6.65 (s, 1), 6.60 (s, 1), 5.20 (m, 1), 4.64 (m, 1), 4.45 (d, 1, J=3 Hz), 3.14 (s, 3), 2.21 (s, 6), 2.16 (s, 6), 2.14 (s, 6), 2.12 (s, 6), 1.11 (s, 9), 0.11 (s, 3), 0.11 (s, 3); $^{31}P$ NMR δ121.1 (d, 1 $J_{pp}$=2 Hz), 113.1 (d, 1, $J_{pp}$=2 Hz); [VIB]Rh OTf ($C_6D_6$) ABX (=PPRh), $\eta_A$=123.6, $\eta_B$=128.2, $J_{AB}$ (JPP)=34, $J_{RhP}$=173. [VIB]Ph(COD)$BF_4$ $^{31}P(C_6D_6)$ ABX (=PPRh) $\eta_A$=124.9, $\eta_B$=127.4, $J_{AB}$=33, $J_{Rh,P}$=173.

VII. Ligands and catalysts from methyl-5,6-O-triphenylmethyl-α-D-fructofuranoside

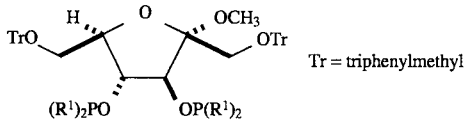

Tr = triphenylmethyl

VIIA. (3,4-diphenylphosphinite), $R^1$=Ph: $^1H$ NMR ($C_6D_6$) 3.10 (s, 3H), 3.35, 3.45 (ABX, $J_{AB}$=10, $J_{AX}$=7, $J_{BX}$=6, 2H), 3.60, 378 (AB, $J_{AB}$=10, 2H), 4.50 (ddm, br, 1H), 4.88 (m, 1H), 5.00 (d, J=10, 1H), 6.80–7.80 (m, aromatic); $^{31}P$ NMR ($C_6D_6$) 114.2, 115.1 (AB, $J_{PP}$=9). [VIIA]Rh$SbF_6$ ($C_6D_6$) ABX (=PPRh), $\eta_A$=119.7, $\eta_B$=122.8 $J_{AB}$ ($J_{PP}$)=29, $J_{RhP}$=166.

VIIB. (3,4-Di-(bis-3,5-dimethylphenyl)phosphinite), $R^1$=3,5-$(CH_3)_2C_6H_3$: $^1H$ NMR δ1.85, 1.91, 1.94, 2.05 (4Xs, 3H each), 3.10 (s, 3H), 3.45–3.60 (ABX, $J_{AB}$=9, $J_{AX}$=$J_{BX}$=5, 2H), 3.67, 3.80 (ABq, JAB=10, 2H), 4.47 (qm, br, 1H), 5.63 (d, J=11 Hz, 1H), 5.20 (m, 1H), 6.50–7.80 (m, aromatic); $^{31}P$ NMR ($C_6D_6$) δ116.41 (d, $J_{PP}$=8, 1 P), 118.53 (d, $J_{PP}$=8, 1 P).

[VIIB]Rh(COD)$BF_4$: $^{31}P$ NMR($C_6D_6$): 114.2 (dd, $J_{RhP}$= 169, $J_{PP}$=28, 1 P), 131.5 (dd, $J_{RhP}$=169, $J_{PP}$=28, 1 P).

VIIC. (3,4-Di-(4-methoxyphenyl)phosphinite), $R^1$=4-($CH_3O)C_6H_4$: $^1H$ NMR ($C_6D_6$) 3.05–3.30 (4×s total 15H), 3.40, 3.50 (ABX, $J_{AB}$=10, $J_{AX}$=7, $J_{BX}$=6, 2H), 3.61, 3.79 (AB, $J_{AB}$=10, 2H), 4.58 (ddm, br, 1H), 4.90 (m, 1H), 5.05 (d, J=10, 1H), 6.42–7.61 (m, aromatic); $^{31}P$ NMR ($C_6D_6$) 115.0, 115.2 (AB, $J_{PP}$=7). [VIIC]Rh(COD)$SbF_6$ ($C_6D_6$) ABX (=PPRh), $\eta_A$=121.8, $\eta_B$=122.1, $J_{AB}$ (=$J_{PP}$)=27, $J_{RhP}$=167; [VIIC]Rh(COD)OTf ($C_6D_6$) ABX (=PPRh), $\eta_A$=121.3, $\eta_B$=121.9, $J_{AB}$ (=$J_{PP}$)=28, $J_{RhP}$=166.

VIII. Ligands and catalysts from 2-naphthyl 4,6-O-benzylidene-β-D-glucopyranoside

VIIIA. (2,3-diphenylphosphinite), $R^1$=Ph: $^1H$ NMR 3.25 (dt, J=8, 4, 1H), 3.35 (t, J=9, 1H), 3.51 (t, J=9, 1H), 4.00 (dd, J=8, 4, 1H), 4.40–4.60 (m, 2H), 4.85 (s, 1H), 5.02 (d, J=8, 1H), 6.50–7.52 (m, aromatic). [VIIA]Rh(COD)$SbF_6$ $^{31}P$ NMR($CDCl_3$): ABX (=$P_1P_2$Rh), $\eta_A$=137.9, $\eta_B$=139.2, $J_{AB}$= 21 Hz, $J_{AX}$=$J_{BX}$ (=$J_{RhP}$)=192 Hz Asymmetric Hydrogenation Reactions:

General Procedure for Scouting Reactions. In the dry box, a 150 mL Fisher-Porter tube was charged with 50 mg of acetamidoacrylate derivative, 1 mg of L*Rh(COD)A, and 1 mL of solvent (THF, MeOH, DME, etc.). The tube was sealed and charged with $H_2$ (10–100 psi). After 3 h, the tube was vented. When $Z^3$=$CH_3$, the crude product was analyzed directly by GC (25 m×0.25 mm Chiralsil L-VAL capillary column) for enantiomeric excess determination. In the case of $Z^3$=H, the crude product was treated with diazomethane prior to analysis by GC. Pure samples of the amino acid derivatives were obtained by recrystallization or by flash chromatography and characterized by $^1H$ NMR.

Synthesis of D-amino acid derivatives (R-configuration)

Examples 1–56 provide D-amino acids under the hydrogenation conditions described above.

TABLE 1

Hydrogenation of Dehydroamino Acid Derivatives
[$Z^1Z^2$C=C($CO_2Z^3$)($NHZ^4$), $Z^1$ = H, $Z^4$ = Ac]
Using L*Rh(COD)A[a]

| Ex. | Cat. | $Z^2$ | $Z^3$ | % ee (R-) | Conditions[a] |
|---|---|---|---|---|---|
| 1 | [IIA]Rh(COD)$BF_4$ | $C_6H_5$ | $CH_3$ | 80.2 | |
| 2 | [IIA]Rh(COD)$BF_4$ | $C_6H_5$ | $CH_3$ | 84 | run at - 10° C. |
| 3 | [IIB]Rh(COD)$BF_4$ | $C_6H_5$ | $CH_3$ | 92.4 | |
| 4 | [IIB]Rh(COD)$BF_4$ | $C_6H_5$ | $CH_3$ | 94.5 | run at - 10° C. |
| 5 | [IIF]Rh(COD)$BF_4$ | $C_6H_5$ | $CH_3$ | 11 | |
| 6 | [IIH]Rh(COD)$BF_4$ | $C_6H_5$ | $CH_3$ | 93.1 | |
| 7 | [IIA]Rh(COD)$BF_4$ | $C_6H_5$ | $CH_3$ | 39.8 | run in MeOH |
| 8 | [IIB]Rh(COD)$BF_4$ | $C_6H_5$ | $CH_3$ | 91.4 | run in DME |
| 9 | [IIB]Rh(COD)$BF_4$ | $C_6H_5$ | $CH_3$ | 88.1 | run in Toluene |
| 10 | [IIB]Rh(COD)$BF_4$ | $C_6H_5$ | $CH_3$ | 87.6 | run in $Bu_2O$ |
| 11 | [IIB]Rh(COD)$BF_4$ | $C_6H_5$ | $CH_3$ | 76.4 | run in EtOH |
| 12 | [IIB]Rh(COD)$BF_4$ | $C_6H_5$ | $CH_3$ | 74.5 | run in MeOH |
| 13 | [IIH]Rh(COD)$BF_4$ | $C_6H_5$ | $CH_3$ | 88.4 | run in $Bu_2O$ |
| 14 | [IIH]Rh(COD)$BF_4$ | $C_6H_5$ | $CH_3$ | 88.2 | run in Toluene |
| 15 | [IIH]Rh(COD)$BF_4$ | $C_6H_5$ | $CH_3$ | 92.4 | run in DME |
| 16 | [IIH]Rh(COD)$BF_4$ | $C_6H_5$ | $CH_3$ | 80.0 | run in EtOH |
| 17 | [IIH]Rh(COD)$BF_4$ | $C_6H_5$ | $CH_3$ | 79.0 | run in MeOH |
| 18 | [IIB]Rh(COD)$BF_4$ | $C_6H_5$ | H | 94.5 | |
| 19 | [IIB]Rh(COD)$BF_4$ | 4-$FC_6H_4$ | $CH_3$ | 92.0 | |
| 20 | [IIB]Rh(COD)$BF_4$ | 3-(MeO)$C_6H_4$ | $CH_3$ | 93.1 | |
| 21 | [IIB]Rh(COD)$BF_4$ | 2-Napth | $CH_3$ | 92.0 | |
| 22 | [IIB]Rh(COD)$BF_4$ | 2-Napth | H | 93.0 | |
| 23 | [IIIA]Rh(COD)$BF_4$ | $C_6H_5$ | $CH_3$ | 58.7 | |
| 24 | [IIIB]Rh(COD)$BF_4$ | $C_6H_5$ | $CH_3$ | 93.0 | |
| 25 | [IIIC]Rh(COD)$BF_4$ | $C_6H_5$ | $CH_3$ | 84.7 | |
| 26 | [IIIE]Rh(COD)$BF_4$ | $C_6H_5$ | $CH_3$ | 1.0 | |
| 27 | [IIIF]Rh(COD)$BF_4$ | $C_6H_5$ | $CH_3$ | 2.3 | |

TABLE 1-continued

Hydrogenation of Dehydroamino Acid Derivatives
[$Z^1Z^2C=C(CO_2Z^3)(NHZ^4)$, $Z^1 = H$, $Z^4 = Ac$]
Using L*Rh(COD)A[a]

| Ex. | Cat. | $Z^2$ | $Z^3$ | % ee (R-) | Conditions[a] |
|---|---|---|---|---|---|
| 28 | [IIIG]Rh(COD)BF$_4$ | C$_6$H$_5$ | CH$_3$ | 2.0 | |
| 29 | [IIIB]Rh(COD)SbF$_6$ | C$_6$H$_5$ | CH$_3$ | 96.0 | |
| 30 | [IIIB]Rh(COD)BF$_4$ | C$_6$H$_5$ | CH$_3$ | 94.0 | run in DME |
| 31 | [IIB]Rh(COD)BF$_4$ | C$_6$H$_5$ | CH$_3$ | 77.9 | run in MeOH |
| 32 | [IIIB]Rh(COD)BF$_4$ | C$_6$H$_5$ | CH$_3$ | 87.6 | run in Toluene |
| 33 | [IIIB]Rh(COD)BF$_4$ | C$_6$H$_5$ | H | 95.8 | |
| 34 | [IIIB]Rh(COD)SbF$_6$ | C$_6$H$_5$ | H | 97.0 | |
| 35 | [IIIB]Rh(COD)SbF$_6$ | 4-FC$_6$H$_4$ | CH$_3$ | 96.2 | |
| 36 | [IIIB]Rh(COD)BF$_4$ | 4-FC$_6$H$_4$ | CH$_3$ | 80.2 | run in MeOH |
| 37[b] | [IIIB]Rh(COD)SbF$_6$ | 4-FC$_6$H$_4$ | CH$_3$ | 90[c] | |
| 38 | [IIIB]Rh(COD)BF$_4$ | 4-FC$_6$H$_4$ | H | 95.4 | |
| 39 | [IIIB]Rh(COD)SbF$_6$ | 4-FC$_6$H$_5$ | H | 96.4 | |
| 40 | [IIIB]Rh(COD)SbF$_6$ | (CH$_3$)$_2$CH | H | 89.2 | |
| 41 | [IIIB]Rh(COD)SbF$_6$ | 3-thienyl | CH$_3$ | 97.0 | |
| 42 | [IVA]Rh(COD)BF$_4$ | C$_6$H$_5$ | CH$_3$ | 94.9 | |
| 43 | [IVB]Rh(COD)BF$_4$ | C$_6$H$_5$ | CH$_3$ | 98.3 | |
| 44 | [IVA]Rh(COD)BF$_4$ | C$_6$H$_5$ | H | 94.5 | |
| 45 | [IVB]Rh(COD)BF$_4$ | C$_6$H$_5$ | H | 94.5 | |
| 46 | [IVB]Rh(COD)BF$_4$ | 4-FC$_6$H$_4$ | CH$_3$ | 97.8 | |
| 47 | [VA]Rh(COD)BF$_4$ | C$_6$H$_5$ | CH$_3$ | 55.4 | |
| 48 | [VA]Rh(COD)BF$_4$ | C$_6$H$_5$ | CH$_3$ | 18.1 | run in MeOH |
| 49 | [VB]Rh(COD)BF$_4$ | C$_6$H$_5$ | CH$_3$ | 72.2 | |
| 50 | [VIB]Rh(COD)OTf | C$_6$H$_5$ | CH$_3$ | 76.0 | |
| 51 | [VIB]Rh(COD)BF$_4$ | C$_6$H$_5$ | CH$_3$ | 65.1 | |
| 52 | [VIIA]Rh(COD)SbF$_6$ | C$_6$H$_5$ | CH$_3$ | 48.0 | |
| 53 | [VIIC]Rh(COD)SbF$_6$ | C$_6$H$_5$ | CH$_3$ | 51 | |
| 54 | [VIIA]Rh(COD)SbF$_6$ | C$_6$H$_5$ | H | 51.0 | |
| 55 | [VIIA]Rh(COD)SbF$_6$ | 4-FC$_6$H$_4$ | CH$_3$ | 53.0 | |
| 56 | [VIIB]Rh(COD)BF$_4$ | 4-FC$_6$H$_4$ | CH$_3$ | 56.8 | |
| 57 | [VIIC]Rh(COD)SbF$_6$ | 4-FC$_6$H$_4$ | CH$_3$ | 57.0 | |

[a]Reaction performed at ambient temperature in THF under 40 psi of H$_2$ pressure unless noted.
[b]In this case, $Z^4 = C(O)OCH_2Ph$ (Cbz).
[c]EE determined on alcohol after reduction of crude product with LiBH$_4$.

Synthesis of L-amino acid derivatives (S-configuration)

Examples 57–98 provide L-amino acids under the hydrogenation conditions described above.

TABLE 2

Hydrogenation of Dehydroamino Acid Derivatives
[$Z^1Z^2C=C(CO_2Z^3)(NHZ^4)$, $Z^1 = H$, $Z^4 = Ac$]
Using L*Rh(COD)A[a]

| Ex. | Cat. | $Z^2$ | $Z^3$ | % ee(S-) | Remarks[a] |
|---|---|---|---|---|---|
| 57 | [IB]Rh(COD)SbF$_6$ | C$_6$H$_5$ | CH$_3$ | 96 | |
| 58 | [IE]Rh(COD)SbF$_6$ | C$_6$H$_5$ | CH$_3$ | 2.0 | |
| 59 | [IG]Rh(COD)BF$_4$ | C$_6$H$_5$ | CH$_3$ | 9.8 | |
| 60 | [IA]Rh(COD)SbF$_6$ | C$_6$H$_5$ | H | 94.0 | |
| 61 | [IB]Rh(COD)SbF$_6$ | C$_6$H$_5$ | H | 99 | |
| 62 | [IC]Rh(COD)SbF$_6$ | C$_6$H$_5$ | H | 93.0 | |
| 63 | [IC]Rh(COD)OTf | C$_6$H$_5$ | H | 96.0 | |
| 64 | [ID]Rh(COD)SbF$_6$ | C$_6$H$_5$ | H | 91 | |
| 65 | [IE]Rh(COD)SbF$_6$ | C$_6$H$_5$ | H | 60 | |
| 66 | [IF]Rh(COD)SbF$_6$ | C$_6$H$_5$ | H | 71 | |
| 67 | [IJ]Rh(COD)SbF$_6$ | C$_6$H$_5$ | H | 47.0 | |
| 68 | [IA]Rh(COD)SbF$_6$ | 4-FC$_6$H$_4$ | CH$_3$ | 84.0 | |
| 69 | [IA]Rh(COD)BF$_4$ | 4-FC$_6$H$_4$ | CH$_3$ | 85.0 | |
| 70 | [IB]Rh(COD)SbF$_6$ | 4-FC$_6$H$_4$ | CH$_3$ | 97.2 | |
| 71 | [IC]Rh(COD)SbF$_6$ | 4-FC$_6$H$_4$ | CH$_3$ | 89 | |
| 72 | [ID]Rh(COD)SbF$_6$ | 4-FC$_6$H$_4$ | CH$_3$ | 81.0 | |
| 73 | [IE]Rh(COD)SbF$_6$ | 4-FC$_6$H$_4$ | CH$_3$ | 13 | |
| 74 | [IF]Rh(COD)SbF$_6$ | 4-FC$_6$H$_4$ | CH$_3$ | 9 | |
| 75 | [IB]Rh(COD)SbF$_6$ | 4-FC$_6$H$_4$ | CH$_3$ | 96.7 | run in EtOH |
| 76 | [IB]Rh(COD)SbF$_6$ | 4-FC$_6$H$_4$ | H | 98.0 | |
| 77[b] | [IA]Rh(COD)SbF$_6$ | 4-FC$_6$H$_4$ | CH$_3$ | 62[c] | |
| 78[b] | [IB]Rh(COD)SbF$_6$ | 4-FC$_6$H$_4$ | CH$_3$ | 97.0[c] | |
| 79[b] | [IC]Rh(COD)SbF$_6$ | 4-FC$_6$H$_4$ | CH$_3$ | 85.0[c] | |
| 80[b] | [IF]Rh(COD)SbF$_6$ | 4-FC$_6$H$_4$ | CH$_3$ | 54[c] | |
| 81 | [IB]Rh(COD)SbF$_6$ | 3-(MeO)C$_6$H$_4$ | CH$_3$ | 98.1 | |

TABLE 2-continued

Hydrogenation of Dehydroamino Acid Derivatives
[$Z^1Z^2C=C(CO_2Z^3)(NHZ^4)$, $Z^1$ = H, $Z^4$ = Ac]
Using L*Rh(COD)A[a]

| Ex. | Cat. | $Z^2$ | $Z^3$ | % ee(S-) | Remarks[a] |
|---|---|---|---|---|---|
| 82 | [IE]Rh(COD)SbF$_6$ | 3-(MeO)C$_6$H$_4$ | CH$_3$ | 21.0 | |
| 83 | [IA]Rh(COD)SbF$_6$ | 3-(MeO)C$_6$H$_4$ | H | 91 | |
| 84 | [IB]Rh(COD)SbF$_6$ | 3-(MeO)C$_6$H$_4$ | H | 97.0 | |
| 85 | [IE]Rh(COD)SbF$_6$ | 3-(MeO)C$_6$H$_4$ | H | 53.0 | |
| 86 | [IF]Rh(COD)SbF$_6$ | 3-(MeO)C$_6$H$_4$ | H | 5 | |
| 87 | [IA]Rh(COD)BF$_4$ | 2-Napth | H | 94.2 | |
| 88 | [IB]Rh(COD)SbF$_6$ | 2-Napth | H | 97.9 | |
| 89 | [IB]Rh(COD)SbF$_6$ | 4-BrC$_6$H$_4$ | H | 98 | |
| 90 | [IE]Rh(COD)SbF$_6$ | 4-BrC$_6$H$_4$ | H | 47 | |
| 91 | [IA]Rh(COD)SbF$_6$ | (CH$_3$)$_2$CH | H | 90.0 | |
| 92 | [IB]Rh(COD)SbF$_6$ | (CH$_3$)$_2$CH | H | 91.0 | |
| 93 | [IC]Rh(COD)SbF$_6$ | (CH$_3$)$_2$CH | H | 83.3 | |
| 94 | [IF]Rh(COD)SbF$_6$ | (CH$_3$)$_2$CH | H | 26.0 | |
| 95 | [IA]Rh(COD)SbF$_6$ | 3-thienyl | CH$_3$ | 86.6 | |
| 96 | [IB]Rh(COD)SbF$_6$ | 3-thienyl | CH$_3$ | 96.7 | |
| 97 | [VIIIA]Rh(COD)SbF$_6$ | C$_6$H$_5$ | H | 89 | |
| 98 | [VIIIA]Rh(COD)SbF$_6$ | 3-(MeO)C$_6$H$_4$ | H | 89.0 | |

[a]Reaction performed at ambient temperature in THF under 40 psi of H$_2$ pressure unless noted.
[b]In this case, $Z^4$ = C(O)OCH$_2$Ph (Cbz).
[c]EE determined on alcohol after reduction of crude product with LiBH$_4$.

Hydrogenation using Ir catalyst

A solution of 50 mg (0.23 mmol) of methyl acetamidocinnamte and 1 mg of [IA]Ir(COD)BF$_4$ in 1 mL of THF was placed in a Fisher-Porter tube in the drybox. This material was charged with 30 psi of H$_2$ pressure and heated to 100° C. The pressure rose to 50 psi. After 3 h, the tube was vented and analyzed as usual. A 7.7% ee (enriched with S-isomer) was obtained.

What is claimed is:

1. A process for asymmetric hydrogenation, comprising: reacting a dehydroamino acid derivative of formula I $$ZZC=C(CO_2Z)(NHZ) \qquad I$$

wherein each Z is independently H or a C$_1$ to C$_{40}$ carboalkoxy, C$_1$ to C$_{40}$ aromatic or nonaromatic hydrocarbyl or C$_1$ to C$_{40}$ aromatic or nonaromatic heterocyclic radical; optionally substituted with one or more halo, alkoxy, carboalkoxy, nitro, haloalkyl, hydroxy, amido, keto or sulfur containing groups;

with a source of hydrogen; in the presence of a catalyst composition comprising iridium or rhodium and a chiral, nonracemic diphosphinite ligand of formula II $$(R^1)_2-P-X-R^2-X-P-(R^1)_2 \qquad II$$

wherein R$^2$ is a C$_4$ to C$_{40}$ dideoxycarbohydrate;
each X is independently O or NR$^3$, wherein R$^3$ is H, C$_1$ to C$_{20}$ alkyl or aryl; and
each R$^1$ is independently an aromatic hydrocarbyl substituted with one or more amino, dialkylamino, hydroxy, alkoxy, alkyl, trialkylsilyl, trialkyaryl groups or an aromatic heterocycle substituted with one or more amino, dialkylamino, hydroxy, alkoxy, alkyl, trialkylsilyl, or triarylsilyl groups; to yield a chiral, nonracemic mixture of compounds of formula III $$ZZCH-CH(CO_2Z)(NHZ) \qquad III$$

wherein Z is defined as above.

2. The process of claim 1 wherein in formula II, the X groups are attached to R$^2$ in a Right-Left diphosphinite configuration, whereby the asymmetric hydrogenation process selectively yields compounds of formula III in S-configuration.

3. The process of claim 1 wherein in formula II, the X groups are attached to R$^2$ in a Left-Right diphosphinite configuration, whereby the asymmetric hydrogenation process selectively yields compounds of formula III in R-configuration.

4. The process of claim 1 wherein the catalyst compositions comprises rhodium, and X is O.

5. The process of claim 1 wherein the dehydroamino acid derivatives of formula I are selected from α-acetamidocinnamic acid and its methyl ester; 2-acetamido-3-(4-fluorophenyl)-prop-2-enoic acid and its methyl ester, 2-acetamido-3-(3-methoxyphenyl)-prop-2-enoic acid and its methyl ester, methyl 2-acetamido-3-(4-trifluoromethylphenyl)-prop-2-enoate, methyl 2-acetamido-3-(4-methoxyphenyl)-prop-2-enoic acid and its methyl ester, methyl 2-acetamido-3-(4-bromophenyl)-prop-2-enoic acid, methyl 2-N-benzyloxycarbonyl-3-(4-fluorophenyl)-prop-2-enoate, 2-acetamidoacrylic acid, 2-acetamido-3-isopropylacrylic acid, 2-acetamido-3-(2-naphthyl)prop-2-enoic acid and its methyl ester, and methyl 2-acetamido-3-(3-thienyl)prop-2-enoate.

6. The process of claim 2 wherein R$^2$ of formula II is selected from 2,3-dideoxyglucose; 2,3-dideoxyxylose; 2,3-dideoxyarabinose; 2,3-dideoxymaltose; 2,3-dideoxymannose; 2,3-dideoxyyallose; 2,3-dideoxylactose; or their corresponding amino sugars.

7. The process of claim 2 wherein the catalyst composition comprises rhodium, R$^2$ of formula II is 2,3-dideoxyglucopyranose, each X is O and each R$^1$ is independently an alkyl or alkoxy substituted phenyl.

8. The process of claim 3 wherein the R$^2$ of formula II is selected from 3,4-dideoxyglucose; 3,4-dideoxyfructose; 3,4-dideoxymannose; 3,4-dideoxyxylose; 3,4-dideoxyarabinose; 3,4-dideoxymaltose; 3,4-dideoxylactose; or their corresponding amino sugars.

9. The process of claim 3 wherein the catalyst composition comprises rhodium, R$^2$ of formula II is 3,4-dideoxyglucopyranose, each X is O, and each R$^1$ is independently an alkyl or alkoxy substituted phenyl.

10. A process for asymmetric hydrogenation, comprising reacting a dehydroamino acid derivative of formula I $$ZZC=C(CO_2Z)(NHZ) \qquad I$$

wherein each Z is independently H or a $C_1$ to $C_{40}$ carboalkoxy, $C_1$ to $C_{40}$ aromatic or nonaromatic hydrocarbyl or $C_1$ to $C_{40}$ aromatic or nonaromatic heterocyclic radical, optionally substituted with one or more halo, alkoxy, carboalkoxy, nitro, haloalkyl, hydroxy, amido, keto or sulfur containing groups;

with a source of hydrogen;

in the presence of a catalyst composition comprising iridium or rhodium and a chiral nonracemic diphosphinite ligand of formula II $$(R^1)_2-P-X-R^2-X-P-(R^1)_2 \qquad II$$

wherein $R^2$ is a $C_4$ to $C_{40}$ dideoxycarbohydrate;

each X is independently O or $NR^3$, wherein $R^3$ is H, a $C_1$ to $C_{20}$ alkyl or aryl; and each $R^1$ is an unsubstituted aromatic hydrocarbyl to, yield a chiral, nonracemic mixture of compounds of formula III $$ZZCH-CH(CO_2Z)(NHZ) \qquad III$$

wherein Z is defined as above;

and wherein in formula II the X groups are attached to $R^2$ in the Left-Right diphosphinite configuration whereby the asymmetric hydrogenation process selectively yields compounds of formula III in R-configuration.

11. The process of claim 10 wherein each $R^1$ is phenyl.

* * * * *